United States Patent
Igawa et al.

(10) Patent No.: US 7,704,609 B2
(45) Date of Patent: Apr. 27, 2010

(54) COMPOUND AND ORGANIC ELECTROLUMINESCENSE DEVICE USING THE SAME

(75) Inventors: Satoshi Igawa, Fujisawa (JP); Shinjiro Okada, Isehara (JP); Takao Takiguchi, Chofu (JP); Jun Kamatani, Tokyo (JP); Masashi Hashimoto, Kawasaki (JP); Hironobu Iwawaki, Atsugi (JP); Kengo Kishino, Yokohama (JP); Minako Kurokawa, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 532 days.

(21) Appl. No.: 11/135,394

(22) Filed: May 24, 2005

(65) Prior Publication Data

US 2006/0003171 A1    Jan. 5, 2006

(30) Foreign Application Priority Data

Jun. 15, 2004    (JP)    ............................. 2004-176556

(51) Int. Cl.
    *H01L 51/54*    (2006.01)
(52) U.S. Cl. .................. 428/690; 428/917; 313/504; 313/506
(58) Field of Classification Search .................. 428/690, 428/917; 427/58, 66; 313/502–509; 257/40, 257/88–103, E51.001–E51.052; 252/301.16–301.35; 585/400–489
See application file for complete search history.

(56) References Cited

U.S. PATENT DOCUMENTS

| | | | |
|---|---|---|---|
| 6,992,437 B2 * | 1/2006 | Lee et al. ..................... | 313/504 |
| 2002/0177009 A1 * | 11/2002 | Suzuki et al. ............... | 428/690 |
| 2005/0276994 A1 * | 12/2005 | Iwawaki et al. ............. | 428/690 |
| 2006/0066225 A1 * | 3/2006 | Kishino et al. .............. | 313/504 |
| 2006/0097227 A1 | 5/2006 | Okajima et al. ........ | 252/301.16 |
| 2007/0122652 A1 * | 5/2007 | Hashimoto et al. .......... | 428/690 |
| 2007/0184302 A1 * | 8/2007 | Iwawaki et al. ............. | 428/690 |

FOREIGN PATENT DOCUMENTS

| | | |
|---|---|---|
| JP | 2003-229273 | 8/2003 |
| JP | 2004-43349 | 2/2004 |
| WO | WO 99/54385 | 10/1999 |
| WO | WO 2004020387 | * 3/2004 |

OTHER PUBLICATIONS

Baldo, et al., "Very High-efficiency Green Organic Light-emitting Devices Based on Electrophosphorescence"; Appl. Phys. Lett., vol. 75, No. 1, pp. 4-6 (1999).
Vincett, et al., "Electrical Conduction and Low Voltage Blue Electroluminescence in Vacuum- deposited Organic Films"; Thin Solid Films, vol. 94, pp. 171-183 (1982).
Kajigaeshi, et al., "Halogenation Using Quaternary Ammonium Polyhalides. XIV. Aromatic Bromination and Iodination of Arenes by Use of Benzyltrimethylammonium Polyhalides-Zinc Chloride System"; Bull. Chem. Soc. Japan., vol. 62, pp. 439-443 (1989).
Burroughes, et al., "Light-emitting Diodes Based on Conjugated Polymers"; Lett. To Nature, vol. 347, pp. 539-541 (1990).
Kauffman, et al., "Electronic Absorption and Emission Spectral Data and Fluorescence Quantum Yields of Bridged p-Oligophenylenes, Bi- to Deciphenyls, and Related Furans and Carbazoles"; Journal of Fluorescence, vol. 5, No. 3, pp. 295-305 (1995).
Chen, et al., "Recent Developments in Molecular Organic Electroluminescent Materials"; Macromol. Symp., vol. 125, pp. 1-48 (1997).
O'Brien, et al., "Improved Energy Transfer in Electrophosphorescent Devices"; Appl. Phys. Lett., vol. 74, No. 3, pp. 442-444 (1999).

* cited by examiner

*Primary Examiner*—Dawn Garrett
(74) *Attorney, Agent, or Firm*—Fitzpatrick, Cella, Harper & Scinto

(57) ABSTRACT

A compound represented by the following general formula (1).

$$R_3-(X)_x-(A)_a-(Y)_y-(B)_b-(Z)_z-R_{12} \qquad (1)$$

(A, B, X, Y, and Z represent the following general formulae, and CH on a phenylene ring of each of X, Y, and Z may be replaced with an N atom. a, b, x, y, and z each independently represent an integer of 0 to 5, and $a \geq 1$, $y \geq 1$, and $a+b \geq 2$.

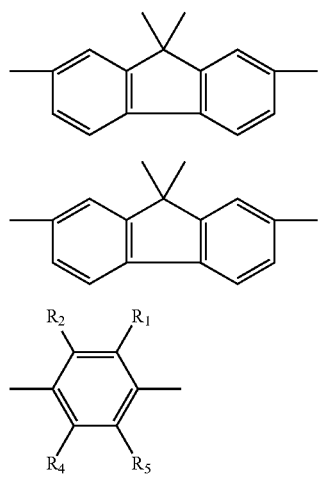

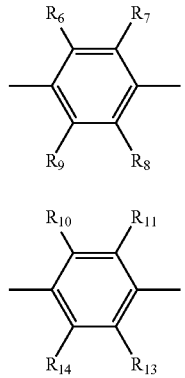

($R_1$ to $R_{14}$ each independently represent a hydrogen atom, or a linear or branched alkyl group.)). The compound can be suitably used as a compound for an organic EL device.

1 Claim, 1 Drawing Sheet

COMPOUND AND ORGANIC ELECTROLUMINESCENSE DEVICE USING THE SAME

BACKGROUND OF THE INVENTION

1. Field of the Invention

The present invention relates to a light emitting device using an organic compound, and more particularly to a novel compound having a specific molecular structure and an organic electroluminescence (EL) device using the same.

2. Related Background Art

In an old example of an organic light emitting device, a voltage is applied to an anthracene evaporated film to emit light (Thin Solid Films, 94 (1982), 171). However, in recent years, applied research including material development has been vigorously made for making a light emitting device which can easily have an increased area as compared to an inorganic light emitting device, which can provide desired color development owing to development of various new materials, which has, for example, an advantage in that it can be driven at a low voltage, and which has high speed responsiveness and high efficiency.

For example, as detailed in Macromol. Symp. 125, 1 to 48 (1997), an organic EL device is generally structured to have two (upper and lower) electrodes formed on a transparent substrate and an organic substance layer including a light emission layer formed between the electrodes.

In addition, investigation has been recently made into a device using not only light emission utilizing fluorescence upon transition from a singlet exciton to a ground state but also phosphorescence emission via a triplet exciton typified by Improved energy transfer in electrophosphorescent device (D. F. O'Brien et al, Applied Physics Letters Vol 74, No 3, p 442 (1999)) and Very high-efficiency green organic light emitting devices based on electrophosphorescence (M. A. Baldo et al, Applied Physics Letters Vol 75, No 1, p 4 (1999)). In each of those documents, an organic layer having a four-layer structure is mainly used. The structure is composed of a hole transport layer, a light emission layer, an exciton diffusion prevention layer, and an electron transport layer from an anode side. The materials used are carrier transport materials and a phosphorescence emission compound Ir(ppy)$_3$ shown below.

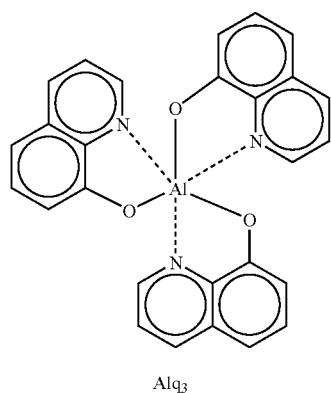

Alq$_3$

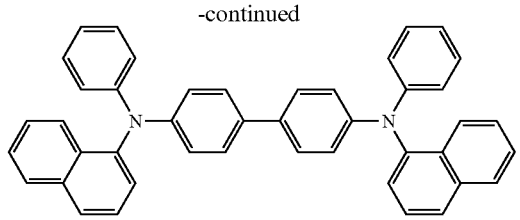

α-NPD

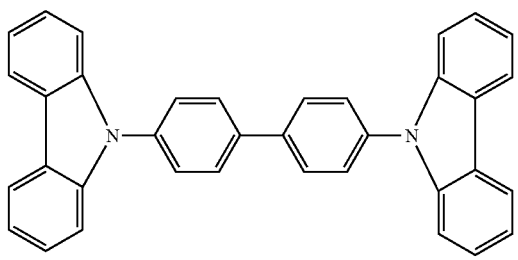

CBP

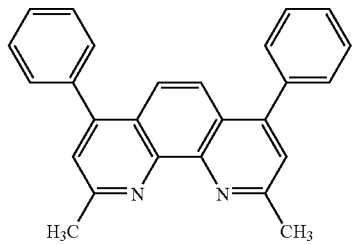

BCP

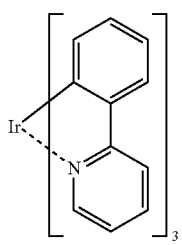

Ir(ppy)$_3$

In addition, light emission from ultraviolet to infrared can be performed by changing the kind of a fluorescent organic compound. In these days, research has been actively made on various compounds.

In addition to organic light emitting devices using such low-molecular materials as those described above, a group of the University of Cambridge has reported organic light emitting devices using conjugate polymers (Nature, 347, 539 (1990)). This report has confirmed that light emission can be obtained by a single layer by forming polyphenylene vinylene (PPV) into a film according to a coating system.

As described above, recent progress of an organic light emitting device is remarkable, and is characterized in that a high responsive, thin, and lightweight light emitting device that can be driven at a low applied voltage and provides high luminance and a variety of luminous wavelengths can be made. Therefore, the progress proposes the potential of the organic light emitting device to find use in a wide variety of applications.

However, at present, an optical output having higher luminance, or higher conversion efficiency has been required. In addition, there still remain a large number of problems in terms of durability such as a change with time due to long-term use and deterioration due to an atmospheric gas containing oxygen or to moisture. Furthermore, light emission of blue, green, or red having a good color purity is necessary when application to a full-color display or the like is attempted. However, those problems have not been sufficiently solved yet.

In addition, a large number of aromatic compounds and condensed polycyclic aromatic compounds have been studied as fluorescent organic compounds used for an electron transport layer, a light emission layer, and the like. However, it is hard to say that a compound sufficiently satisfying light emission luminance and durability has been already obtained.

Examples of a patent document describing application of a fluorene compound relating to the present invention to an organic EL include Japanese Patent Application Laid-Open No. 2004-43349, International Publication No. WO 99/54385, and Japanese Patent Application Laid-Open No. 2003-229273. However, none of the patent documents discloses an organic compound of the present invention characterized by including a partial structure containing a fluorene ring and a phenylene ring on a straight line in a molecular structural formula. In addition, a fluorene compound has been reported as application to laser coloring matter (Journal of Fluorescence, Vol. 5, No. 3, 295 (1995)).

An organic EL device must have an optical output of high efficiency and high luminance and sufficiently secure high durability when the device is to be applied to a display device such as a display. However, such an optical output and high durability have not been sufficiently achieved.

SUMMARY OF THE INVENTION

An object of the present invention is to provide a novel compound that can be suitably used as a compound for an organic EL device. Another object of the present invention is to provide an organic EL device using the compound and having an optical output of high efficiency and high luminance. Another object of the present invention is to provide an organic EL device with high durability. Another object of the present invention is to provide an organic EL device that can be produced easily and at a relatively low cost.

That is, according to one aspect of the present invention, there is provided a compound represented by the following general formula (1):

(A, B, X, Y, and Z represent the following general formulae, and CH on a phenylene ring of each of X, Y, and Z may be replaced with an N atom. a, b, x, y, and z each independently represent an integer of 0 to 5, and $a \geq 1$, $y \geq 1$, and $a+b \geq 2$.

A

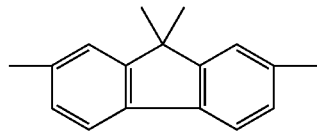

B

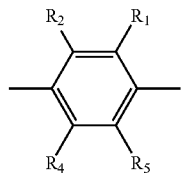

X

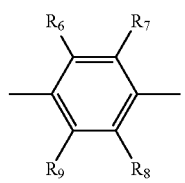

Y

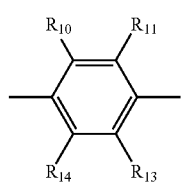

Z ($R_1$ to $R_{14}$ each independently represent a hydrogen atom, or a linear or branched alkyl group.))

According to another aspect of the present invention, there is provided an organic electroluminescence device including: a pair of electrodes; and at least one layer containing an organic compound sandwiched between the electrodes, in which the at least one layer containing an organic compound contains the compound represented by the general formula (1).

The compound of the present invention has a high glass transition temperature, and the light emitting device of the present invention using the compound of the present invention as a host of a light emission layer is an excellent device which is capable of emitting light at high efficiency and maintains high luminance for a long period of time. In addition, the light emitting device has an increased current value at the same voltage value, so it is expected to be driven at a low voltage.

DESCRIPTION OF THE PREFERRED EMBODIMENTS

Figure 1A:
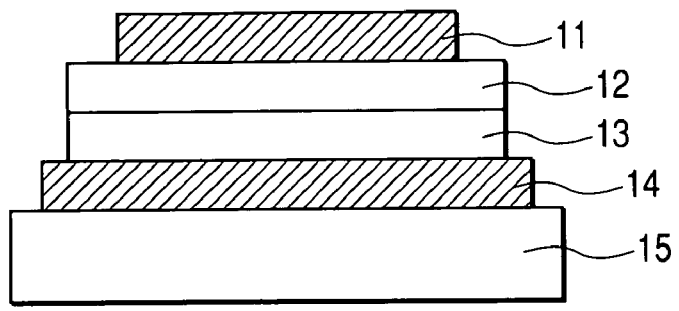
FIGS. 1A, 1B and 1C each are drawing showing examples of a light emitting device of the present invention.

First, the compound of the present invention will be described.

When a light emission layer is composed of a carrier transport host material and a guest, a main route to light emission is composed of the following several steps.

1. transport of an electron and a hole in the light emission layer
2. generation of an exciton of the host 3. transfer of excitation energy between host molecules
4. movement of excitation energy from the host to the guest Desired energy movement and light emission in the respective steps are caused by various deactivation steps and competition.

It is needless to say that the luminescent quantum yield of a light emitting center material itself must be large in order to increase the luminous efficiency of an EL device. However, the efficiency of energy movement between a host and another host or between a host and a guest is also a large problem. In addition, a cause for deterioration of light emission due to energization has not been clarified yet. However, the deterioration is probably related to at least environmental changes to a light emitting material due to the light emitting center material or molecules around the center material.

In view of the above, the inventors of the present invention have made various studies to find that a device using the compound represented by the general formula (1) as a host of a light emission layer maintains high luminance for a long period of time, and shows small deterioration due to energization.

One possible cause for the deterioration of light emission due to energization is the deterioration of light emission due to the deterioration of a thin film shape of the light emission layer. The deterioration of the thin film shape probably results from the temperature of an environment where the device is driven and the crystallization of an organic thin film due to, for example, heat generation at the time of driving the device. This probably results from the low glass transition temperature of the material, and an organic EL material is requested to have a high glass transition temperature. The compound of the present invention represented by the general formula (1) has a high glass transition temperature, and is expected to provide the organic EL device with high durability.

Of those, a compound represented by the following general formula (2), (3), (4), or (5) is preferable.

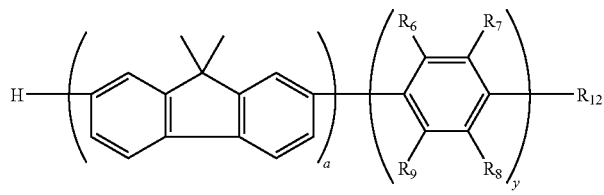

(2)

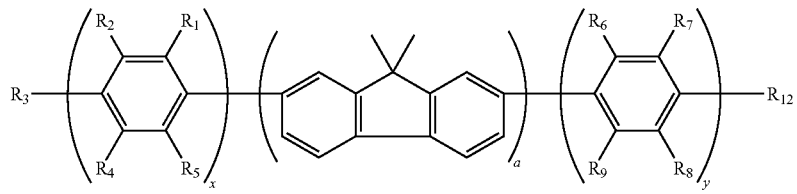

(3)

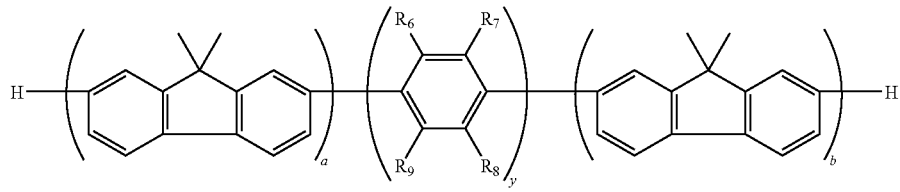

(4)

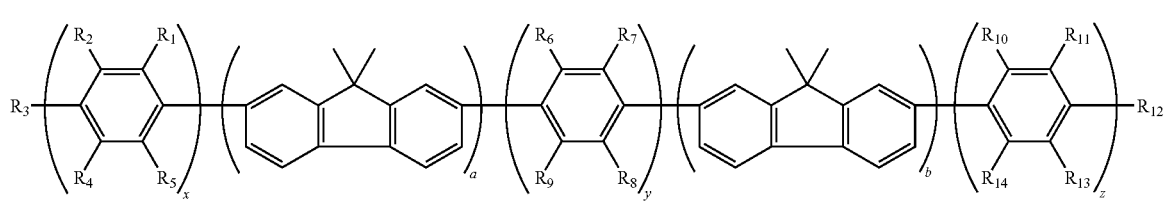

(5)

($b \geq 1$, $x \geq 1$, and $z \geq 1$)

In the compound of the present invention, when an alkyl chain at position 9 of the fluorene group is lengthened, the glass transition temperature is expected to reduce. In the case where position 9 of the fluorene group is a methyl group, the compound has a higher glass transition temperature and high heat resistance, and is hence expected to provide the organic EL device with high durability. In addition, $R_1$ to $R_{14}$ of substituents are each preferably a hydrogen atom or a methyl group in terms of the glass transition temperature.

Another possible cause for the deterioration of light emission due to energization is contamination of impurities. When a polymer compound is used for the device, it is difficult to remove the impurities in the polymer compound. As a result, the impurities are apt to contaminate the device, thereby causing a reduction in lifetime of the device. Since the compound of the present invention is a single compound, appropriate use of a purification method such as recrystallization, column chromatography, or sublimation purification facilitates the removal of the impurities and is expected to provide the organic EL device with high durability.

A driving voltage must be low in order to obtain a device having high luminous efficiency. To achieve this, it is important to provide a host with charge conductivity. In terms of conductivity, when the alkyl chain at position 9 of the fluorene group of the general formula (1) is lengthened, the charge conductivity is expected to reduce. In the case where position 9 of the fluorene group is a methyl group, the host has higher charge conductivity, the driving voltage of the device can be reduced, and hence the efficiency of the organic EL device is expected to increase. In addition, $R_1$ to $R_{14}$ of substituents are each preferably a hydrogen atom or a methyl group in terms of the charge conductivity as well.

In addition, conventionally known fluorescent materials and phosphorescent materials can be used for guest molecules when the compound of the present invention is used as the host of the light emission layer. To obtain a light emitting device having high efficiency, metal complexes such as an Ir complex, a Pt complex, an Re complex, a Cu complex, an Eu complex, and an Rh complex known to emit phosphorescence are preferably used. An Ir complex known to emit strong phosphorescence is more preferably used. Furthermore, multiple phosphorescence emitting materials may be incorporated into the light emission layer for the purposes of developing multiple colors from the light emission layer and aiding the transfer of an exciton and charge.

An organic layer containing the compound of the present invention can be produced by means of vacuum vapor deposition, casting, application, spin coating, an inkjet method, or the like.

Specific structural formulae of the organic compound used in the present invention are shown below, provided, however, that they are merely representative examples and the present invention is not limited to them.

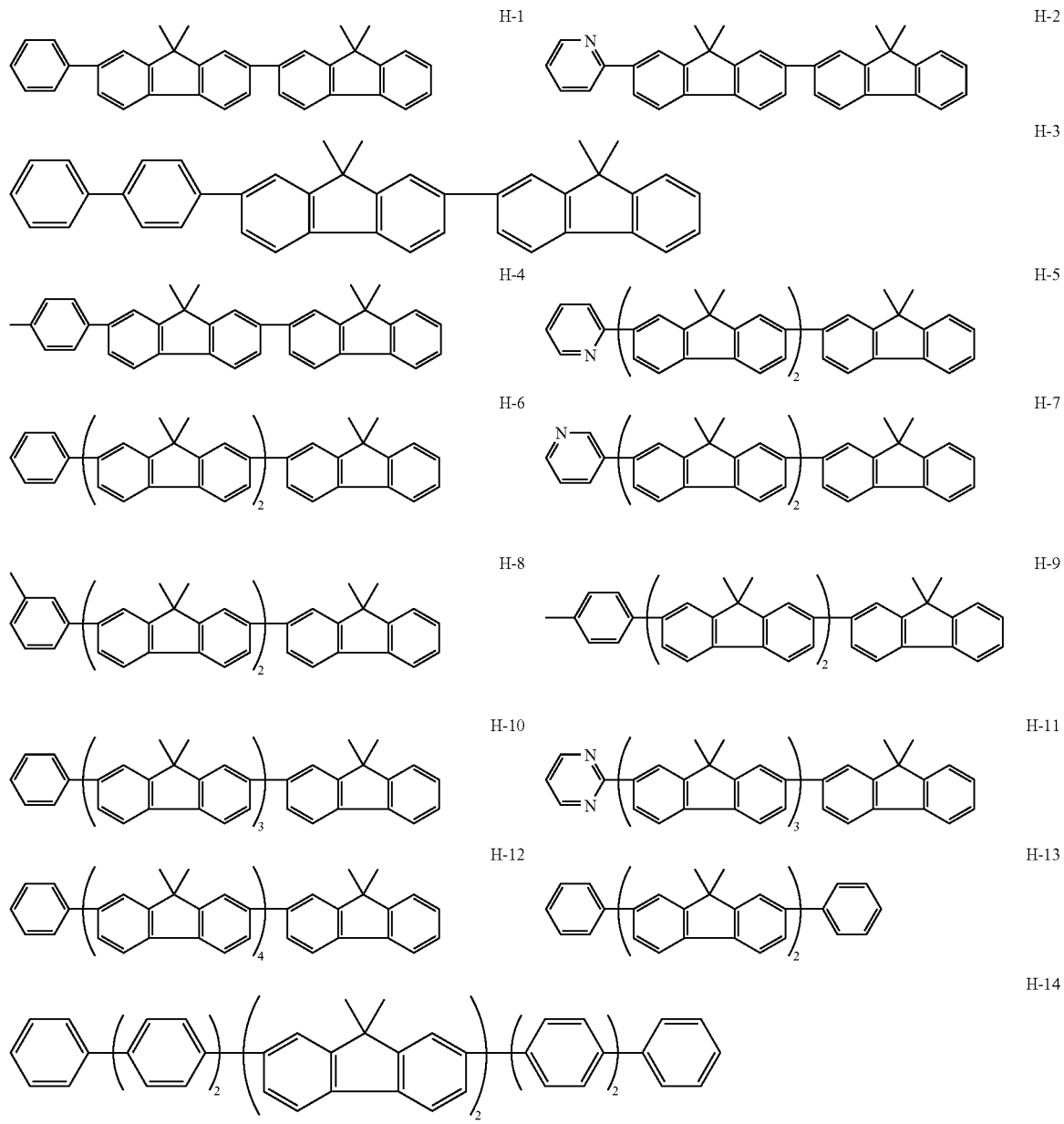

-continued
H-15
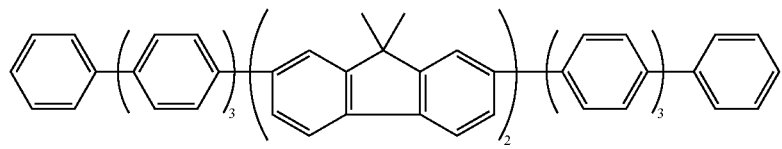
H-16
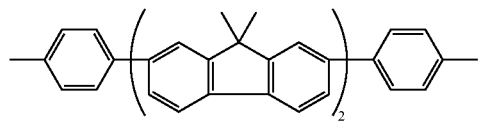
H-17
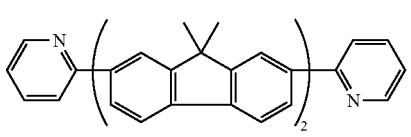
H-18
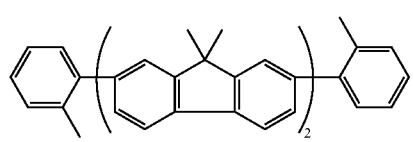
H-19
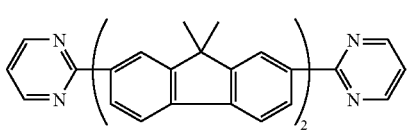
H-20
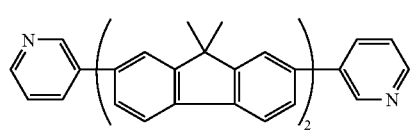
H-21
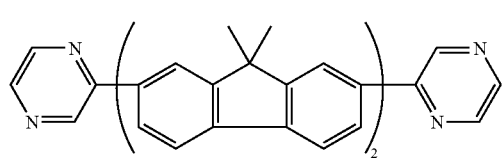
H-22
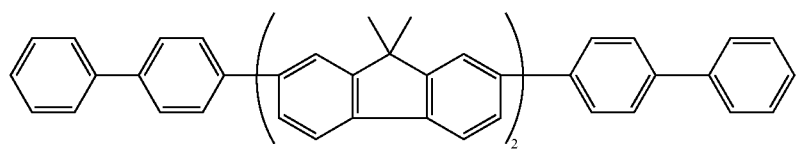
H-23
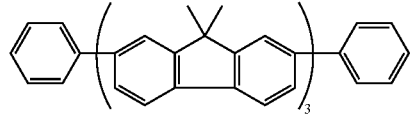
H-24
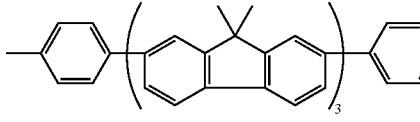
H-25
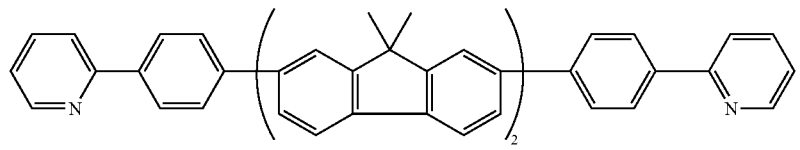
H-26
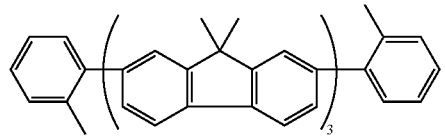
H-27
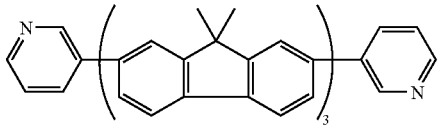
H-28
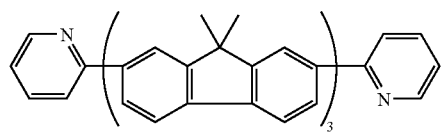
H-29
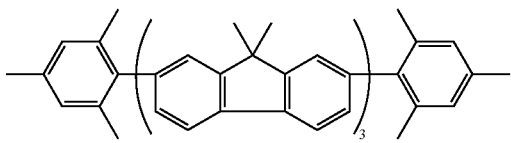
H-30
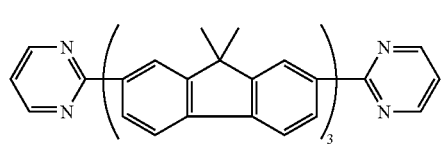
H-31
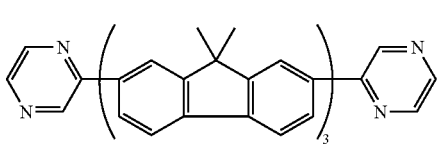
H-32

-continued
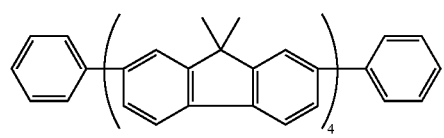 H-33
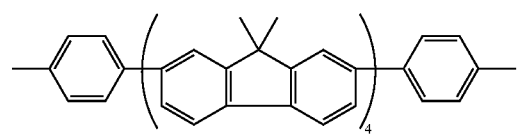 H-34
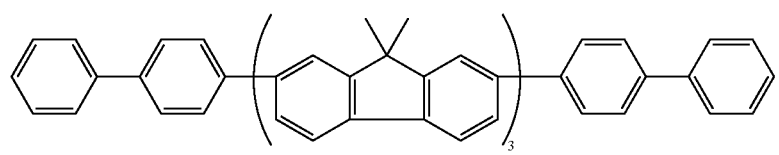 H-35
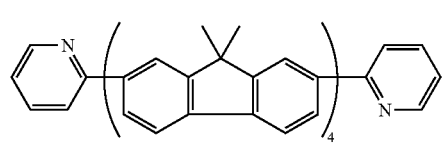 H-36
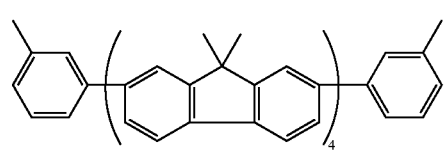 H-37
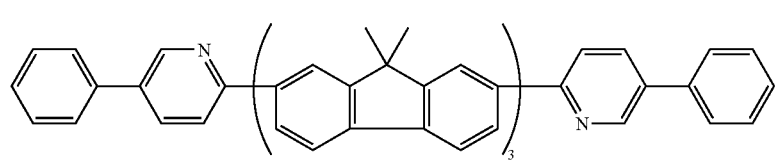 H-38
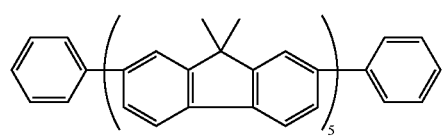 H-39
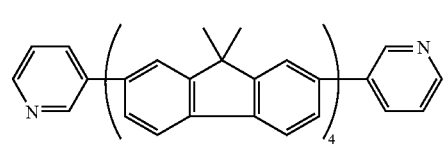 H-40
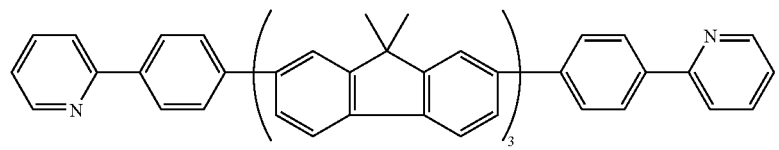 H-41
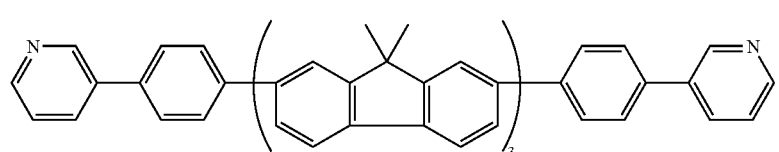 H-42
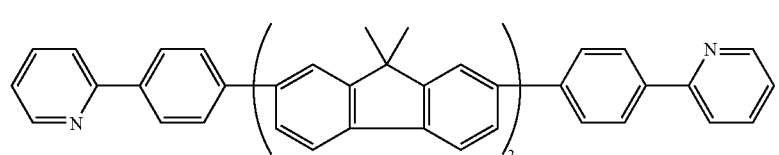 H-43
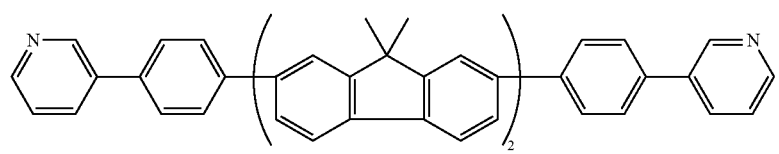 H-44
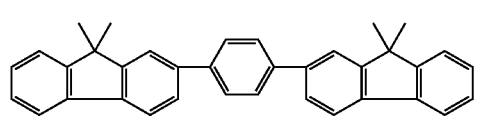 H-45
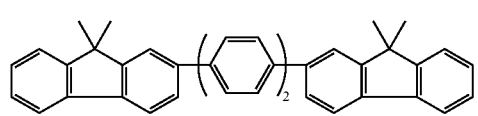 H-47
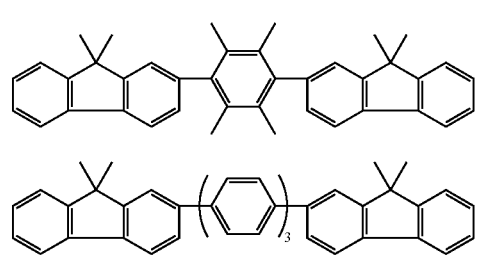 H-46 H-48

-continued
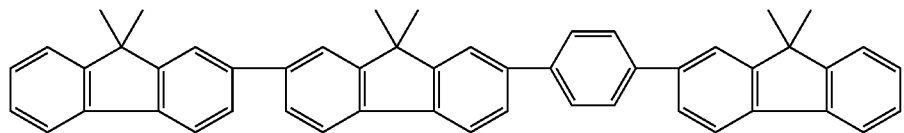
H-49
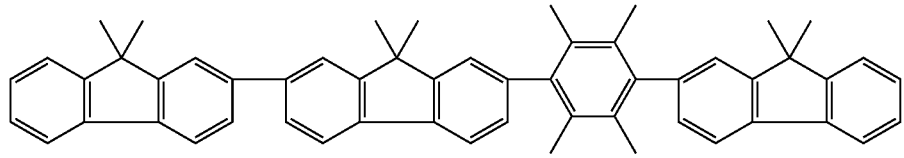
H-50
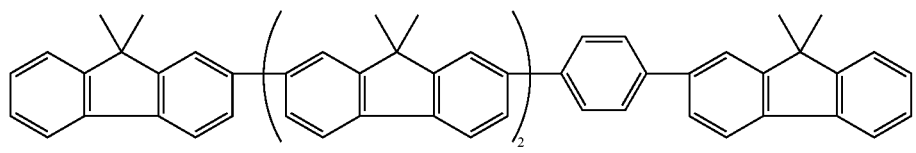
H-51
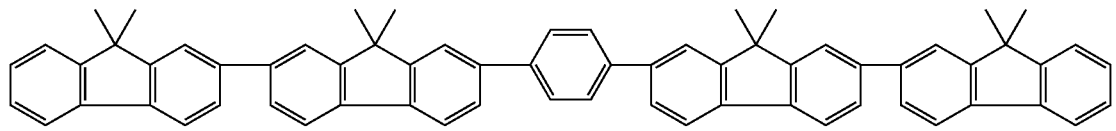
H-52
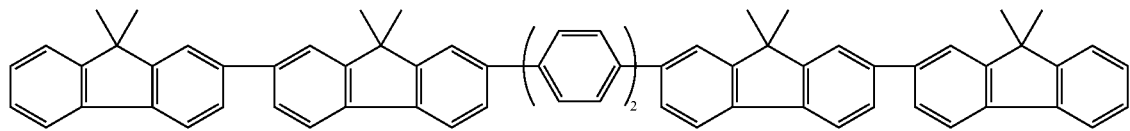
H-53
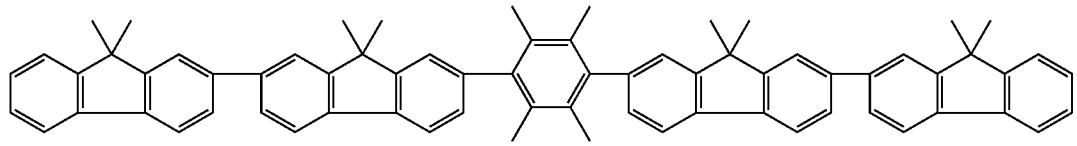
H-54
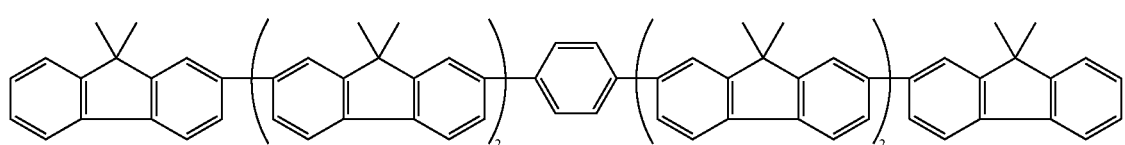
H-55
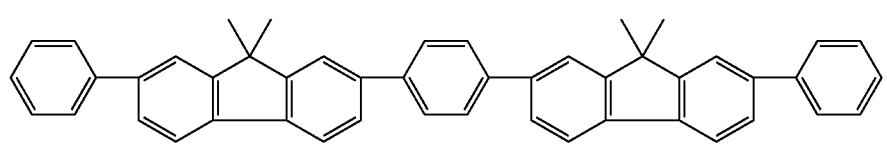
H-56
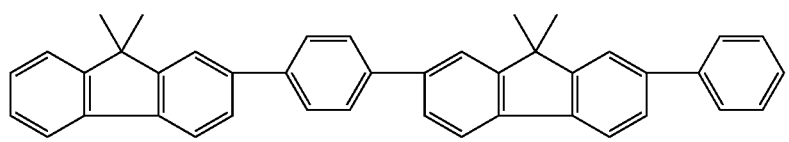
H-57
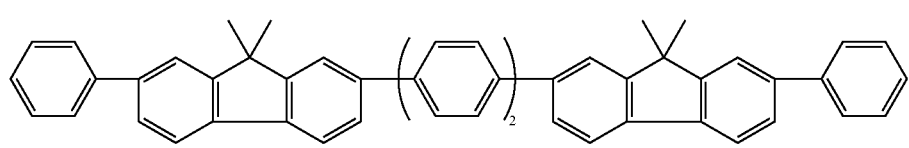
H-58

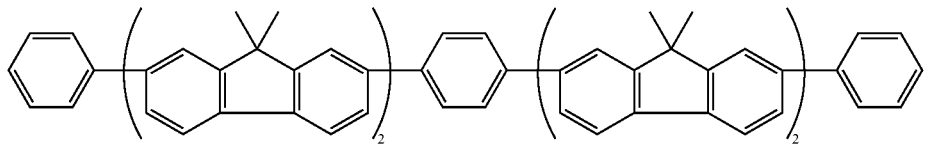

H-59

Next, a light emitting device of the present invention will be described.

Figure 1B:
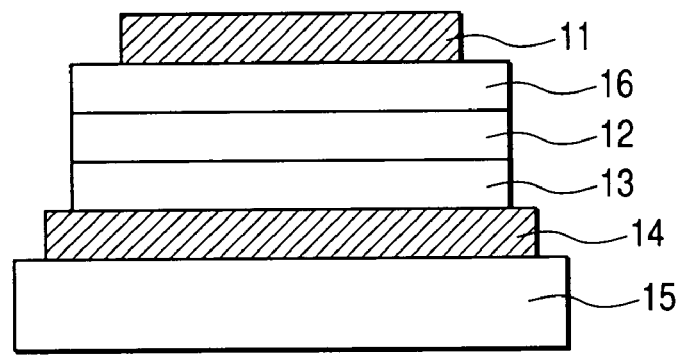
Figure 1C:
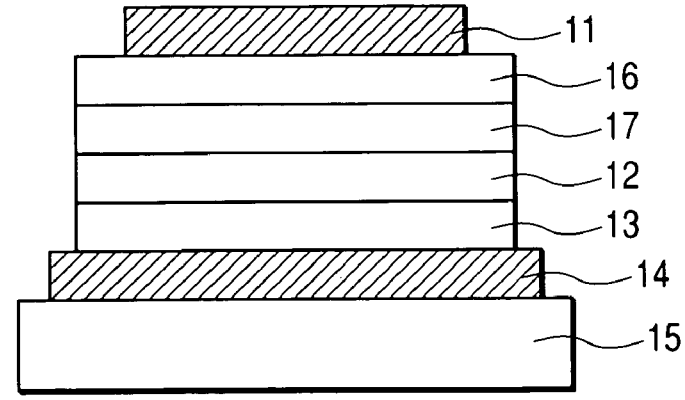

FIGS. 1A to 1C each show the basic structure of the device of the present invention.

As shown in FIGS. 1A to 1C, an organic EL device generally includes: a transparent substrate 15; a transparent electrode 14 having a thickness of 50 to 200 nm on the transparent substrate 15; multiple organic layers on the transparent electrode 14; and a metal electrode 11 to sandwich the multiple organic layers between the transparent electrode 14 and the metal electrode 11.

FIG. 1A shows an example in which the organic layers are composed of a light emission layer 12 and a hole transport layer 13. ITO having a large work function is used for the transparent electrode 14, so a hole can be easily injected from the transparent electrode 14 to the hole transport layer 13. A metal material having a small work function such as aluminum, magnesium, or an alloy using any one of them is used for the metal electrode 11, so electrons can be easily injected to the organic layers.

The compound of the present invention is used for the light emission layer 12. For example, a triphenyl diamine derivative, which is typified by α-NPD, having electron donative property can be appropriately used for the hole transport layer 13.

The device having the structure described above exhibits electrical rectifying property. When an electric field is applied with the metal electrode 11 as a cathode and the transparent electrode 14 as an anode, an electron is injected from the metal electrode 11 to the light emission layer 12, while a hole is injected from the transparent electrode 14.

The injected hole and electron are recombined in the light emission layer 12 to generate an exciton, thereby causing light emission. At this time, the hole transport layer 13 serves as an electron blocking layer. As a result, recombination efficiency at an interface between the light emission layer 12 and the hole transport layer 13 increases to thereby increase the luminous efficiency.

In FIG. 1B, an electron transport layer 16 is arranged between the metal electrode 11 and the light emission layer 12 shown in FIG. 1A. A light emitting function and electron/hole transport functions are separated to establish a more effective carrier blocking structure, whereby the luminous efficiency is increased. An oxadiazole derivative or the like can be used for the electron transport layer 16.

As shown in FIG. 1C, the combination of a four-layer structure composed of the hole transport layer 13, the light emission layer 12, an exciton diffusion prevention layer 17, the electron transport layer 16 and the metal electrode 11 from the side of the transparent electrode 14 as the anode is also desirable. In FIGS. 1B and 1C, the same reference numerals as those of FIG. 1A denote the same members as those of FIG. 1A.

Hereinafter, the present invention will be described specifically by way of examples. However, the present invention is not limited to these examples.

First, the following reaction intermediate was synthesized.

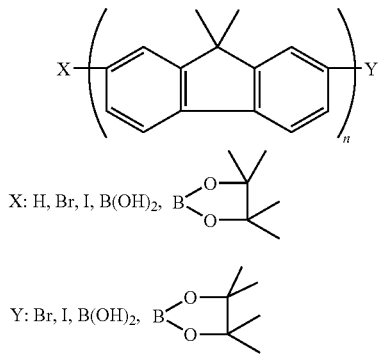

(X and Y each independently represent the above group. n represents an integer of 1 to 5.)

First, 2-halogeno-9H-fluorene and 2,7-dihalogeno-9H-fluorene were synthesized with reference to Bull. Chem. Soc. Jpn. 62 (1989) 439. The resultant compounds were subjected to dimethylation of position 9 of fluorene in DMF using $CH_3Cl$ and $NaOCH_3$. Furthermore, the resultant 2-halogeno-9-dimethylfluorene and 2,7-dihalogeno-9-dimethylfluorene were subjected to synthesis of boric acid or pinacol borate with reference to ORGANIC SYNTHESIS VIA BORANES Volume 3. The resultant compounds were subjected to an appropriate combination of Suzuki coupling (ORGANIC SYNTHESIS VIA BORANES Volume 3), halogenation (Bull. Chem. Soc. Jpn. 62 (1989) 439), and synthesis of boric acid, to thereby synthesize the reaction intermediate.

The compound of the present invention can be synthesized by subjecting an appropriate combination of the fluorene derivative, a halogenated benzene derivative, and a benzene boric acid derivative to a Suzuki coupling reaction.

EXAMPLE 1

Synthesis of Exemplified Compound No. H-52

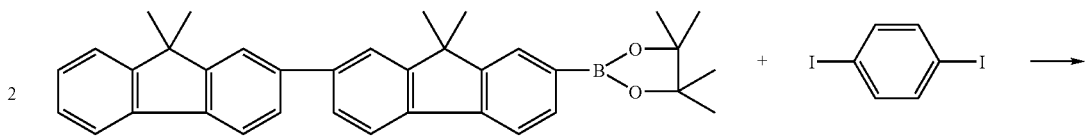

Compound A

-continued

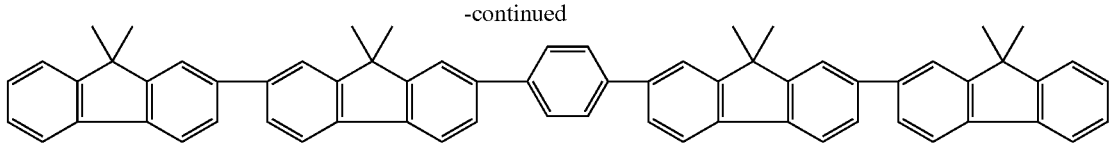

512 mg (1 mmole) of a compound A, 165 mg (0.5 mmole) of 1,4-diiodobenzene, 0.1 g of Pd(PPh$_3$)$_4$, 10 ml of toluene, 5 ml of ethanol, and 10 ml of a 2-M aqueous solution of sodium carbonate were fed into a 100-ml round-bottomed flask, and the whole was stirred for 8 hours at 80° C. in a stream of nitrogen. After the completion of the reaction, the crystal was filtered out and washed with water, ethanol, and toluene. The resultant crystal was dried in a vacuum at 120° C., and was then subjected to sublimation purification to yield 200 mg of Exemplified Compound No. H-52 (47.2% yield).

846.2 as M+ of the compound was observed by means of matrix assisted laser desorption/ionization-time of flight mass spectrometry (MALDI-TOF MS).

In addition, the structure of the compound was identified by NMR measurement.

$^1$H NMR (CDCl$_3$, 400 MHz) σ (ppm): 7.65-7.83 (m, 22H), 7.47 (m, 2H), 7.30-7.37 (m, 4H), 1.68 (s, 12H), 1.60 (s, 12H)

EXAMPLE 2

In this example, a device having three organic layers shown in FIG. 1B was used as a device structure.

ITO (as the transparent electrode 14) having a thickness of 100 nm was patterned on a glass substrate (as the transparent substrate 15). The following organic layers and electrode layers were continuously formed on the ITO substrate by means of vacuum vapor deposition according to resistance heating in a vacuum chamber having a pressure of 10$^{-5}$ Pa, to have an opposing electrode area of 3 mm$^2$. Hole transport layer 13 (20 nm): compound B Light emission layer 12 (50 nm): Exemplified Compound No. H-52: Ir(piq)$_3$ (10% in weight ratio) Electron transport layer 16 (30 nm): Bphen (manufactured by Dojin Laboratories) Metal electrode layer 1 (1 nm): KF Metal electrode layer 2 (100 nm): Al The current-voltage characteristics of the EL device were measured by using a microammeter 4140B manufactured by Hewlett-Packard Development Company, and the light emission luminance thereof was measured by using a BM7 manufactured by Topcon Corporation.

The device of this example had an efficiency of 6.0 cd/A, 5.2 lm/W (600 cd/m$^2$). In addition, the device showed a current value of 251 mA/cm$^2$ when a voltage of 8 V was applied. When continuous energization of 100 mA/cm$^2$ was performed on the device, it took 413 hours to reduce an initial luminance of 4,015 cd/m$^2$ in half.

EXAMPLE 3

Synthesis of Exemplified Compound No. H-47

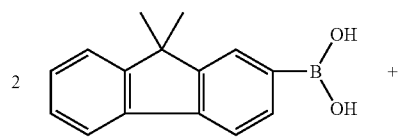 +

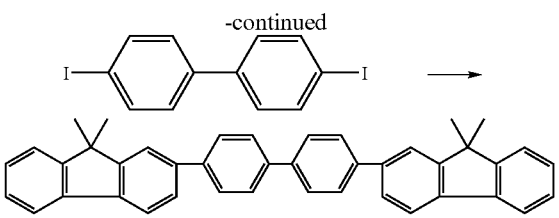

476 mg (2 mmole) of 2-(9,9-dimethyl)-fluorene boric acid, 406 mg (1 mmole) of 4,4'-diiodobiphenyl, 0.2 g of Pd(PPh$_3$)$_4$, 12 ml of toluene, 6 ml of ethanol, and 12 ml of a 2-M aqueous solution of sodium carbonate were fed into a 100-ml round-bottomed flask, and the whole was stirred for 8 hours at 80° C. in a stream of nitrogen. After the completion of the reaction, the reaction solution was extracted with toluene. The organic layer was washed with water and dried with magnesium sulfate, followed by evaporation to dryness under reduced pressure. The resultant was purified by means of silica gel column chromatography (eluent: hexane/toluene=10/1), followed by recrystallization with toluene/hexane. The resultant crystal was dried in a vacuum at 120° C., and was then subjected to sublimation purification to yield 377 mg of Exemplified Compound No. H-47 (70.0% yield).

538.3 as M+ of the compound was observed by means of matrix assisted laser desorption/ionization-time of flight mass spectrometry (MALDI-TOF MS).

In addition, the structure of the compound was identified by NMR measurement.

$^1$H NMR (CDCl$_3$, 400 MHz) σ (ppm): 7.75 (d, 2H), 7.69-7.73 (m, 10H), 7.65 (d, 2H), 7.59 (m, 2H), 7.41 (m, 2H), 7.25-7.34 (m, 4H), 1.50 (s, 12H)

In addition, the compound had a glass transition temperature of 182° C.

EXAMPLE 4

A device was produced in the same manner as in Example 2 except that Exemplified Compound No. H-47 was used instead of Exemplified Compound No. H-52.

The device of this example had an efficiency of 5.0 cd/A, 4.0 lm/W (600 cd/m$^2$). In addition, the device showed a current value of 155 mA/cm$^2$ when a voltage of 8 V was applied. When continuous energization of 100 mA/cm$^2$ was performed on the device, it took 258 hours to reduce an initial luminance of 3,015 cd/m$^2$ in half.

COMPARATIVE EXAMPLE 1

A device was produced in the same manner as in Example 2 except that CBP was used instead of Exemplified Compound No. H-52.

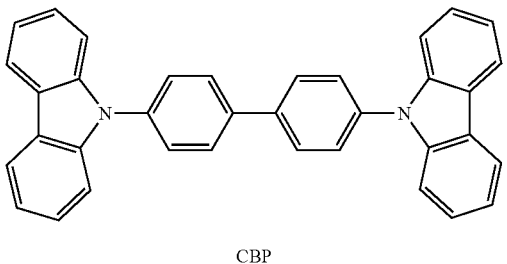

CBP

The device of this example had an efficiency of 6.2 cd/A, 4.2 lm/W (600 cd/m$^2$). In addition, the device showed a current value of 116 mA/cm$^2$ when a voltage of 8 V was applied. When continuous energization of 100 mA/cm$^2$ was performed on the device, it took 156 hours to reduce an initial luminance of 4,022 cd/m$^2$ in half.

Table 1 summarizes the device characteristics of Examples 2 and 4 and Comparative Example 1.

TABLE 1

| | Light emission layer host | Glass transition temperature (° C.) | Efficiency (lm/W) at 600 cd/m$^2$ | Current value (mA/cm$^2$) at 8 V | Half life (h) |
|---|---|---|---|---|---|
| Example 2 | No. H-52 | | 5.2 | 251 | 413 |
| Example 4 | No. H-47 | 182 | 4.0 | 155 | 258 |
| Comparative Example 1 | CBP | 115 | 4.2 | 116 | 156 |

As shown in Table 1, the compound of the present invention has a glass transition temperature higher than that of CBP used as a host of a light emission layer. In addition, an organic EL device using the compound of the present invention as a host of a light emission layer is an excellent device which has power efficiency equal to or higher than that of a device using CBP and a half life about 2 to 3 times as long as that of the device using CBP. In addition, the organic EL device shows a current value about 1.5 to 2 times as high as that of the device using CBP at the same voltage value. Therefore, the organic EL device is extremely excellent also because it can be driven at a low voltage.

EXAMPLE 5

Synthesis of Exemplified Compound No. H-24

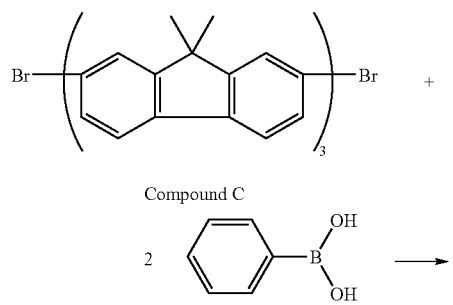

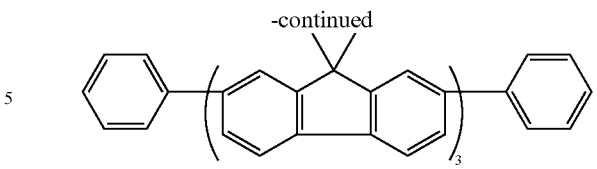

1 g (1.36 mmole) of a compound C, 331 mg (2.72 mmole) of phenyl boric acid, 0.13 g of Pd(PPh$_3$)$_4$, 10 ml of toluene, 5 ml of ethanol, and 10 ml of a 2-M aqueous solution of sodium carbonate were fed into a 100-ml round-bottomed flask, and the whole was stirred for 8 hours at 80° C. in a stream of nitrogen. After the completion of the reaction, the reaction solution was extracted with toluene. The organic layer was washed with water and dried with magnesium sulfate, followed by evaporation to dryness under reduced pressure. The resultant was purified by means of silica gel column chromatography (eluent: hexane/toluene=10/1), followed by recrystallization with toluene/hexane. The resultant crystal was dried in a vacuum at 120° C., and was then subjected to sublimation purification to yield 0.75 g of Exemplified Compound No. H-24 (75.4% yield).

730.4 as M+ of the compound was observed by means of matrix assisted laser desorption/ionization-time of flight mass spectrometry (MALDI-TOF MS).

In addition, the structure of the compound was identified by NMR measurement.

$^1$H NMR (CDCl$_3$, 400 MHz) σ (ppm): 7.85 (m, 6H), 7.66-7.76 (m, 14H), 7.62 (m, 2H), 7.48 (t, 4H), 7.37 (t, 2H), 1.66 (s, 6H), 1.63 (s, 12H)

In addition, the compound had a glass transition temperature of 138° C.

EXAMPLE 6

A device was produced in the same manner as in Example 1 except that: Exemplified Compound No. H-24 was used instead of Exemplified Compound No. H-52; and two compound dopes, that is, Ir(4 mopiq)$_3$ (4% in weight ratio) and Ir(bq)$_3$ (8% in weight ratio), were used instead of Ir(piq)$_3$ (10% in weight ratio).

The device of this example had an efficiency of 14.3 cd/A, 14.0 lm/W (600 cd/m$^2$). In addition, the device showed a current value of 720 MA/cm$^2$ when a voltage of 8 V was applied. When continuous energization of 100 mA/cm$^2$ was performed on the device, it took 265 hours to reduce an initial luminance of 7,953 cd/m in half.

COMPARATIVE EXAMPLE 2

A device was produced in the same manner as in Example 6 except that CBP was used instead of Exemplified Compound No. H-24.

The device of this example had an efficiency of 17.2 cd/A, 12.2 lm/W (600 cd/m$^2$). In addition, the device showed a current value of 140 mA/cm$^2$ when a voltage of 8 V was applied. When continuous energization of 100 mA/cm$^2$ was performed on the device, it took 113 hours to reduce an initial luminance of 8,010 cd/m$^2$ in half.

Table 2 summarizes the device characteristics of Example 6 and Comparative Example 2.

TABLE 2

| | Light emission layer host | Glass transition temperature (°C.) | Efficiency (lm/W) at 600 cd/m$^2$ | Current value (mA/cm$^2$) at 8 V | Half life (h) |
|---|---|---|---|---|---|
| Example 6 | No. H-24 | 138 | 14.0 | 720 | 265 |
| Comparative Example 2 | CBP | 115 | 12.2 | 113 | 140 |

As shown in Table 2, the compound of the present invention has a glass transition temperature higher than that of CBP. In addition, an organic EL device using the compound of the present invention as a host of a light emission layer is an excellent device which has power efficiency higher than that of a device using CBP and a half life about twice as long as that of the device using CBP. In addition, the organic EL device shows a current value about 6 times as high as that of the device using CBP at the same voltage value. Therefore, the organic EL device is extremely excellent also because it can be driven at a low voltage.

EXAMPLE 7

Synthesis of Exemplified Compound No. H-45

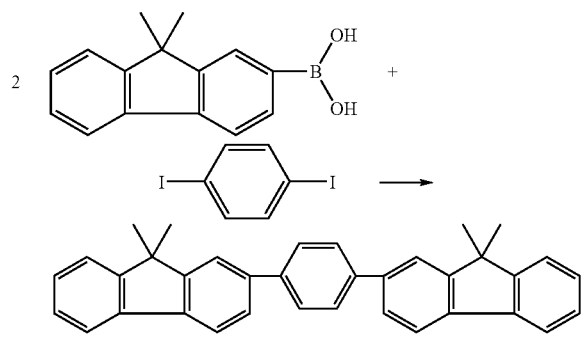

476 mg (2 mmole) of 2-(9,9-dimethyl)-fluoren-2-yl boric acid, 330 mg (1 mmole) of 1,4-diiodobenzene, 0.2 g of Pd(PPh$_3$)$_4$, 12 ml of toluene, 6 ml of ethanol, and 12 ml of a 2-M aqueous solution of sodium carbonate were fed into a 100-ml round-bottomed flask, and the whole was stirred for 8 hours at 80° C. in a stream of nitrogen. After the completion of the reaction, the reaction solution was extracted with toluene. The organic layer was washed with water and dried with magnesium sulfate, followed by evaporation to dryness under reduced pressure. The resultant was purified by means of silica gel column chromatography (eluent: hexane/toluene=10/1), followed by recrystallization with toluene/hexane. The resultant crystal was dried in a vacuum at 120° C., and was then subjected to sublimation purification to yield 339 mg of Exemplified Compound No. H-45 (73.3% yield).

462.2 as M+ of the compound was observed by means of matrix assisted laser desorption/ionization-time of flight mass spectrometry (MALDI-TOF MS).

In addition, the structure of the compound was identified by NMR measurement.

$^1$H NMR (CDCl$_3$, 400 MHz) σ (ppm): 7.81 (d, 2H), 7.77 (m, 6H), 7.71 (d, 2H), 7.65 (m, 2H), 7.47 (m, 2H), 7.31-7.39 (m, 4H), 1.57 (s, 12H)

EXAMPLE 8

Synthesis of Exemplified Compound No. H-25

Exemplified Compound No. H-25 was synthesized in the same manner as in Example 5 except that 4-methylphenyl boric acid was used instead of phenyl boric acid.

EXAMPLE 9

Synthesis of Exemplified Compound No. H-27

Exemplified Compound No. H-27 was synthesized in the same manner as in Example 5 except that 3-methylphenyl boric acid was used instead of phenyl boric acid.

EXAMPLE 10

Synthesis of Exemplified Compound No. H-54

Exemplified Compound No. H-54 was synthesized in the same manner as in Example 1 except that 1,4-diiodo-2,3,5,6-tetramethyl benzene was used instead of 1,4-diiodobenzene.

EXAMPLE 11

Synthesis of Exemplified Compound No. H-29

Exemplified Compound No. H-29 was synthesized in the same manner as in Example 5 except that: a compound D was used instead of the compound C; and 2 equivalents of 2-chloropyridine with respect to the compound D were used instead of phenyl boric acid.

Compound D

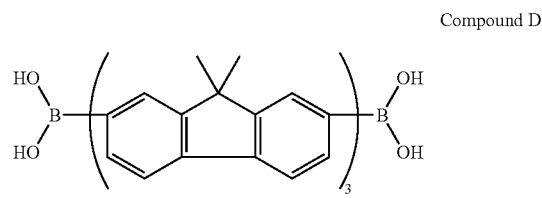

EXAMPLE 12

Synthesis of Exemplified Compound No. H-28

Exemplified Compound No. H-28 was synthesized in the same manner as in Example 11 except that 3-iodopyridine was used instead of 2-chloropyridine.

EXAMPLE 13

Synthesis of Exemplified Compound No. H-6

Exemplified Compound No. H-6 was synthesized in the same manner as in Example 5 except that: a compound E was used instead of the compound C; and 1 equivalent of phenyl boric acid was used with respect to the compound E.

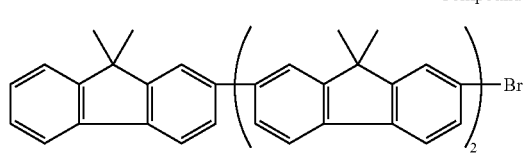

Compound E

EXAMPLE 14

Synthesis of Exemplified Compound No. H-31

Exemplified Compound No. H-31 was synthesized in the same manner as in Example 11 except that 2-chloropyrimidine was used instead of 2-chloropyridine.

EXAMPLE 15

Synthesis of Exemplified Compound No. H-32

Exemplified Compound No. H-32 was synthesized in the same manner as in Example 14 except that 2-chloropyrazine was used instead of 2-chloropyrimidine.

EXAMPLE 16

Synthesis of Exemplified Compound No. H-53

Exemplified Compound No. H-53 was synthesized in the same manner as in Example 1 except that 4,4'-diiodobiphenyl was used instead of 1,4-diiodobenzene.

EXAMPLE 17

Synthesis of Exemplified Compound No. H-5

Exemplified Compound No. H-5 was synthesized in the same manner as in Example 5 except that: a compound F was used instead of the compound C; and 1 equivalent of 2-chloropyridine with respect to the compound F was used instead of 1,4-diiodobenzene.

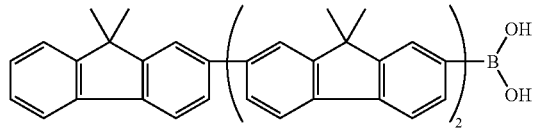

Compound F

EXAMPLE 18

Synthesis of Exemplified Compound No. H-7

Exemplified Compound No. H-7 was synthesized in the same manner as in Example 17 except that 3-iodopyridine was used instead of 2-chloropyridine.

EXAMPLE 19

Synthesis of Exemplified Compound No. H-8

Exemplified Compound No. H-8 was synthesized in the same manner as in Example 13 except that 3-methylphenyl boric acid was used instead of phenyl boric acid.

EXAMPLE 20

Synthesis of Exemplified Compound No. H-9

Exemplified Compound No. H-9 was synthesized in the same manner as in Example 13 except that 4-methylphenyl boric acid was used instead of phenyl boric acid.

EXAMPLE 21

Synthesis of Exemplified Compound No. H-35

Exemplified Compound No. H-35 was synthesized in the same manner as in Example 11 except that 4-iodobiphenyl was used instead of 2-chloropyridine.

EXAMPLE 22

Synthesis of Exemplified Compound No. H-41

Exemplified Compound No. H-41 was synthesized in the same manner as in Example 11 except that 2-(4-bromophenyl)pyridine was used instead of 2-chloropyridine.

EXAMPLE 23

Synthesis of Exemplified Compound No. H-42

Exemplified Compound No. H-42 was synthesized in the same manner as in Example 11 except that 3-(4-bromophenyl)pyridine was used instead of 2-chloropyridine.

EXAMPLE 24

Synthesis of Exemplified Compound No. H-13

Exemplified Compound No. H-13 was synthesized in the same manner as in Example 5 except that a compound G was used instead of the compound C.

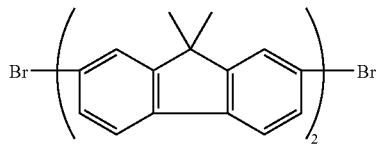

Compound G

EXAMPLE 25

Synthesis of Exemplified Compound No. H-16

Exemplified Compound No. H-16 was synthesized in the same manner as in Example 24 except that 4-methylphenyl boric acid was used instead of phenyl boric acid.

EXAMPLE 26

Synthesis of Exemplified Compound No. H-17

Exemplified Compound No. H-17 was synthesized in the same manner as in Example 24 except that 3-methylphenyl boric acid was used instead of phenyl boric acid.

EXAMPLE 27

Synthesis of Exemplified Compound No. H-18

Exemplified Compound No. H-18 was synthesized in the same manner as in Example 24 except that 2-methylphenyl boric acid was used instead of phenyl boric acid.

EXAMPLE 28

Synthesis of Exemplified Compound No. H-19

Exemplified Compound No. H-19 was synthesized in the same manner as in Example 11 except that a compound H was used instead of the compound D.

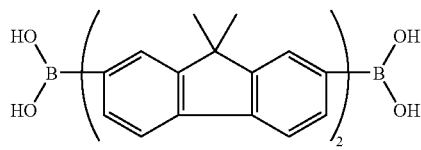

Compound H

EXAMPLE 29

Synthesis of Exemplified Compound No. H-20

Exemplified Compound No. H-20 was synthesized in the same manner as in Example 28 except that 3-iodopyridine was used instead of 2-chloropyridine.

EXAMPLE 30

Synthesis of Exemplified Compound No. H-21

Exemplified Compound No. H-21 was synthesized in the same manner as in Example 28 except that 2-chloropyrimidine was used instead of 2-chloropyridine.

EXAMPLE 31

Synthesis of Exemplified Compound No. H-22

Exemplified Compound No. H-22 was synthesized in the same manner as in Example 28 except that 2-chloropyrazine was used instead of 2-chloropyrizine.

EXAMPLE 32

Synthesis of Exemplified Compound No. H-23

Exemplified Compound No. H-23 was synthesized in the same manner as in Example 28 except that 4-iodobiphenyl was used instead of 2-chloropyridine.

EXAMPLE 33

Synthesis of Exemplified Compound No. H-26

Exemplified Compound No. H-26 was synthesized in the same manner as in Example 28 except that 2-(4-bromophenyl)pyridine was used instead of 2-chloropyridine.

EXAMPLE 34

Synthesis of Exemplified Compound No. H-33

Exemplified Compound No. H-33 was synthesized in the same manner as in Example 5 except that a compound I was used instead of the compound C.

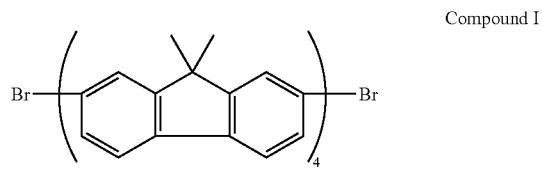

Compound I

EXAMPLE 35

Synthesis of Exemplified Compound No. H-34

Exemplified Compound No. H-34 was synthesized in the same manner as in Example 34 except that 4-methylphenyl boric acid was used instead of phenyl boric acid.

EXAMPLE 36

Synthesis of Exemplified Compound No. H-37

Exemplified Compound No. H-37 was synthesized in the same manner as in Example 34 except that 3-methylphenyl boric acid was used instead of phenyl boric acid.

EXAMPLE 37

Synthesis of Exemplified Compound No. H-36

Exemplified Compound No. H-36 was synthesized in the same manner as in Example 11 except that a compound J was used instead of the compound D.

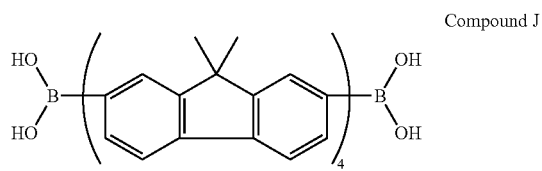

Compound J

EXAMPLE 38

Synthesis of Exemplified Compound No. H-40

Exemplified Compound No. H-40 was synthesized in the same manner as in Example 37 except that 3-iodopyridine was used instead of 2-chloropyridine.

EXAMPLE 39

Synthesis of Exemplified Compound No. H-43

Exemplified Compound No. H-43 was synthesized in the same manner as in Example 37 except that 2-(4-bromophenyl) pyridine was used instead of 2-chloropyridine.

EXAMPLE 40

Synthesis of Exemplified Compound No. H-44

Exemplified Compound No. H-44 was synthesized in the same manner as in Example 37 except that 3-(4-bromophenyl)pyridine was used instead of 2-chloropyridine.

EXAMPLE 41

Synthesis of Exemplified Compound No. H-49

A compound K was synthesized in the same manner as in Example 7 except that 1 equivalent of 1-bromo-4-iodobenzene with respect to 2-(9,9-dimethyl)-fluoren-2-yl boric acid was used instead of 1,4-diiodobenzene. Suzuki coupling between the compound K and a compound L was performed in the same manner as in Example 7 to synthesize Exemplified Compound No. H-49.

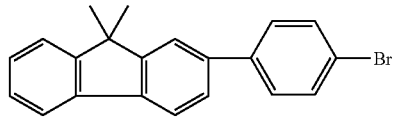

Compound K

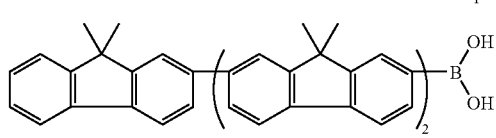

Compound L

This application claims priority from Japanese Patent Application No. 2004-176556 filed Jun. 15, 2004, which is hereby incorporated by reference herein.

What is claimed is:

1. An organic electroluminescence device comprising a pair of electrodes and a layer containing an organic compound sandwiched between the pair of electrodes, wherein the layer containing the organic compound comprises

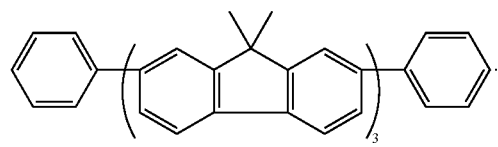

* * * * *